United States Patent
Makino et al.

(12) 
(10) Patent No.: US 6,399,305 B1
(45) Date of Patent: Jun. 4, 2002

(54) PROTECTION OF PARTIAL COMPLEMENTARY NUCLEIC ACID FRAGMENT USING A ELECTROCONDUCTIVE CHIP AND INTERCALATOR

(75) Inventors: Yoshihiko Makino; Yoshihiko Abe, both of Asaka; Makoto Takagi, Fukuoka; Shigeori Takenaka, Koga; Kenichi Yamashita, Fukuoka; Masashi Ogawa, Tokyo, all of (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/588,950

(22) Filed: Jun. 7, 2000

(30) Foreign Application Priority Data

Jun. 7, 1999 (JP) .......................................... 11-159339

(51) Int. Cl.$^7$ ................................................ C12Q 1/68
(52) U.S. Cl. ............................................. 435/6; 436/94
(58) Field of Search ................................ 435/6; 436/94

(56) References Cited

U.S. PATENT DOCUMENTS

| 5,705,348 | A | * | 1/1998 | Meade et al. | ................... 435/6 |
| 6,203,758 | B1 | * | 3/2001 | Marks et al. | ............... 422/68.1 |
| 6,221,586 | B1 | * | 4/2001 | Barton et al. | ................... 435/6 |
| 6,261,780 | B1 | * | 7/2001 | Ogawa et al. | ................... 435/6 |
| 6,294,670 | B1 | * | 9/2001 | Takenaka | ..................... 544/225 |

FOREIGN PATENT DOCUMENTS

JP 409288080 * 11/1997

OTHER PUBLICATIONS

Takenaka, Bull. Chem. Soc. Jpn 74, 217–224 (2001).*

* cited by examiner

Primary Examiner—Kenneth R. Horlick
(74) Attorney, Agent, or Firm—Reed Smith LLP

(57) ABSTRACT

A method of analyzing a nucleic acid fragment sample to judge whether the nucleic acid fragment sample is uncomplementary, partly complementary or complementary to a DNA fragment in its specific base sequence is conducted by the steps of:

bringing an aqueous solution of the nucleic acid fragment sample into contact with a DNA chip having an electroconductive substrate and the DNA fragment fixed onto the substrate in the presence of an electrochemical thread intercalator;

measuring an electric current flowing from or to the electroconductive substrate along the DNA fragment under application of a potential to the substrate; and comparing the electric current measured above with a referential electric current which is prepared employing a DNA chip equivalent to the above DNA chip, the intercalator, and an aqueous solution of a nucleic acid fragment which is complementary to the DNA fragment of the DNA chip.

20 Claims, 6 Drawing Sheets

11a

11b

↓ 31   ↓ 31

21a

21b

SEQUENCE LISTING

<160> NUMBER OF SEQ ID NOS: 9

<210> SEQ ID NO 1
<211> LENGTH: 13
<212> TYPE: DNA
<213> ORGANISM: Artificial Sequence
<220> FEATURE:
<223> OTHER INFORMATION: Synthesized

<400> SEQUENCE: 1
gtcggactga aga                                                              13

<210> SEQ ID NO 2
<211> LENGTH: 13
<212> TYPE: DNA
<213> ORGANISM: Artificial Sequence
<220> FEATURE:
<223> OTHER INFORMATION: Synthesized

<400> SEQUENCE: 2
cagcctgact tct                                                              13

<210> SEQ ID NO 3
<211> LENGTH: 13
<212> TYPE: DNA
<213> ORGANISM: Artificial Sequence
<220> FEATURE:
<223> OTHER INFORMATION: Synthesized

<400> SEQUENCE: 3
gtcggagtga aga                                                              13

<210> SEQ ID NO 4
<211> LENGTH: 13
<212> TYPE: DNA
<213> ORGANISM: Artificial Sequence
<220> FEATURE:
<223> OTHER INFORMATION: Synthesized

<400> SEQUENCE: 4
cagcctcact tct                                                              13

<210> SEQ ID NO 5
<211> LENGTH: 20
<212> TYPE: DNA
<213> ORGANISM: Artificial Sequence
<220> FEATURE:
<223> OTHER INFORMATION: Synthesized

<400> SEQUENCE: 5
tttttttttt attttttttt                                                       20

<210> SEQ ID NO 6

```
-continued

<211> LENGTH: 20
<212> TYPE: DNA
<213> ORGANISM: Artificial Sequence
<220> FEATURE:
<223> OTHER INFORMATION: Synthesized

<400> SEQUENCE: 6
ttttttttaa aattttttttt                                              20

<210> SEQ ID NO 7
<211> LENGTH: 10
<212> TYPE: DNA
<213> ORGANISM: Artificial Sequence
<220> FEATURE:
<223> OTHER INFORMATION: Synthesized

<400> SEQUENCE: 7
ctctcctttt                                                          10

<210> SEQ ID NO 8
<211> LENGTH: 10
<212> TYPE: DNA
<213> ORGANISM: Artificial Sequence
<220> FEATURE:
<223> OTHER INFORMATION: Synthesized

<400> SEQUENCE: 8
aaaagtagag                                                          10

<210> SEQ ID NO 9
<211> LENGTH: 10
<212> TYPE: DNA
<213> ORGANISM: Artificial Sequence
<220> FEATURE:
<223> OTHER INFORMATION: Synthesized

<400> SEQUENCE: 9
aaaaggagag                                                          10
```

PROTECTION OF PARTIAL COMPLEMENTARY NUCLEIC ACID FRAGMENT USING A ELECTROCONDUCTIVE CHIP AND INTERCALATOR

FIELD OF THE INVENTION

This invention relates to a detection of a partly complementary nucleic acid fragment. The detection of a partly complementary nucleic acid fragment is of value in the gene analyses such as analysis of gene polymorphism and analysis of variation of abnormal gene.

BACKGROUND OF THE INVENTION

The gene analysis is recently paid an attention in developing gene technology.

As a representative gene analysis method for detecting variation of gene fragments, SSCP (single-stranded conformation polymorphism) is known. The procedure of SSCP for differentiating an abnormal gene fragment from a normal gene fragment is illustrated in FIG. 1 attached to the specification. Each of double stranded normal gene fragments (11a) and double stranded abnormal gene fragments (11b, which is different from the normal gene fragment 11a in the base unit positioned in the crossed place) is treated (31) to give a set of two single stranded gene fragments (21a, 21b), as illustrated in FIG. 1-(A). Both of the single stranded gene fragments (21a, 21b) are subjected to electrophoresis on a polyacrylamide gel. Each gene fragment has a specific high-order structure differing from each other. Accordingly, each of the single stranded gene fragments (21a, 21b) moves differently from each other in the electrophoresis, as illustrated in FIG. 1-(B). The detection of the movement of the gene fragment gives an information of variation of gene fragments.

The SSCP meth, however, sometimes fails to differentiate an abnormal gene fragment from a normal gene fragment, because a certain abnormal gene fragment moves similarly to the corresponding normal gene fragment. Particularly, if the variation of base takes place in the vicinity of a gene fragment, it is likely that the abnormal gene fragment takes almost the same high-order structure as that of the corresponding normal gene fragment, and hence that there is caused almost no difference of movement in the electrophoresis.

The variation of gene fragment from a single stranded normal gene fragment to a single stranded abnormal gene fragment can be also detected by way of hybridization. In the hybridization, a hybrid structure is formed differently between the normal gene fragment and the abnormal gene fragment.

Japanese Patent PCT Publication 9-501561 describes detection of a double-stranded nucleic acid hybrid having a specific structure by means of a fluorescent microscope.

It is also known that different double-stranded nucleic acid fragment hybrids are detected by temperature graduation gel electrophoresis.

It is known that there are three types of hybrid structures, namely, a full-match structure in which two single stranded DNA fragments are hybridized to form a complete double-stranded DNA fragment;

a mis-match structure in which two single stranded DNA fragments are hybridized to form a double-stranded DNA fragment having one uncoupled base unit, which is generally observed in the case that a normal DNA fragment is hybridized with an abnormal DNA fragment which differs from the normal DNA fragment in one base unit; and a bulge structure in which two single stranded DNA fragments are hybridized to form a double-stranded DNA fragment having two or more uncoupled base units.

Japanese Patent Provisional Publication No. 9-288080 describes a method for detecting a double stranded DNA fragment of a full-match structure by way of an electrochemical detection method. In this method, a sample DNA fragment is electrochemically detected using a DNA probe which is complementary to the sample DNA fragment in the presence of an electrochemically active thread intercalator.

P. E. Nielsen et al., Science, 254, 1497–1500(1991) and P. E. Nielsen et al., Biochemistry, 36, pp.5072–5077 (1997) describe PNA (Peptide Nucleic Acid or Polyamide Nucleic Acid) which has no negative charge and functions in the same manner as DNA does. PNA has a polyamide skeleton of N-(2-aminoethyl)glycine units and has neither glucose units nor phosphate groups. A representative PNA as well as a representative DNA are illustrated below:

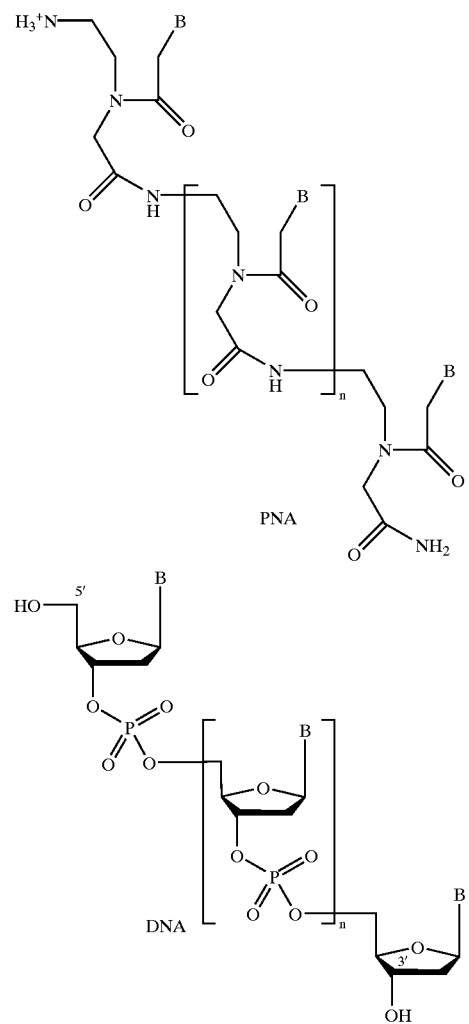

Since PNA is electrically neutral and is not charged in the absence of an electrolytic salt, PNA is able to hybridize with a complementary nucleic acid fragment to form a hybrid which is more stable than hybrid given by a DNA prove and its complementary nucleic acid fragment (Preprint of the 74th Spring Conference of Japan Chemical Society, pp. 1287, reported by Naomi Sugimoto).

Japanese Patent Provisional Publication No.11-332595 describes a PNA probe fixed on a electroconductive substrate at its one end and a detection method utilizing the PNA probe. The PNA probe is fixed onto the electroconductive substrate by the avidin-biotin method.

The aforementioned P. E. Nielsen et al, Science, 254, 1497–1500(1991) also describes a PNA probe labelled with isotope element and a detection method of a complementary nucleic acid fragment.

Since the PNA probe shows no electric repulsion to a target nucleic acid fragment in a sample liquid, an improved high detection sensitivity is expected.

SUMMARY OF THE INVENTION

It is an object of the present invention to provide a method of analyzing a nucleic acid fragment sample to judge whether the nucleic acid fragment sample is uncomplementary, partly complementary, or complementary to a DNA fragment or PNA fragment in its specific base sequence. This analyzing method is of value in the gene analysis such as analysis of gene polymorphism or analysis of variation of abnormal gene.

The present invention resides in a method of analyzing a nucleic acid fragment sample to judge whether the nucleic acid fragment sample is uncomplementary, partly complementary or complementary to a DNA fragment in its specific base sequence, which comprises the steps of:

bringing an aqueous solution of the nucleic acid fragment sample into contact with a DNA chip comprising an electroconductive substrate and the DNA fragment fixed onto the substrate in the presence of an electrochemical thread intercalator;

measuring an electric current flowing from or to the electroconductive substrate along the DNA fragment under application of a potential to the substrate; and comparing the electric current measured above with a referential electric current which is prepared employing a combination of a DNA chip equivalent to the above-mentioned DNA chip, the electrochemical thread intercalator, and an aqueous solution of a nucleic acid fragment which is complementary to the DNA fragment of the DNA chip.

The invention also resides in a method of analyzing a nucleic acid fragment sample to judge whether the nucleic acid fragment sample is uncomplementary, partly complementary or complementary to a PNA fragment in its specific base sequence, which comprises the steps of:

bringing an aqueous solution of the nucleic acid fragment sample into contact with a PNA chip comprising an electroconductive substrate and the PNA fragment fixed onto the substrate in the presence of an electrochemical thread intercalator;

measuring an electric current flowing from or to the electroconductive substrate along the PNA fragment under application of a potential to the substrate; and comparing the electric current measured above with a referential electric current which is prepared employing a combination of a PNA chip equivalent to the above-mentioned PNA chip, the electrochemical thread intercalator, and an aqueous solution of a nucleic acid fragment which is complementary to the PNA fragment of the PNA chip.

The above-defined detection methods of the invention preferably further comprises the steps of:

bringing an aqueous solution not containing the nucleic acid fragment sample into contact with a DNA chip (or a PNA chip) equivalent of the DNA chip (or the PNA chip) in the presence of the electrochemical thread intercalator;

measuring an electric current flowing from or to the electroconductive substrate along the DNA fragment (pr PNA fragment) under application of a potential to the substrate so as to obtain a background electric current; and comparing the background electric current with the electric current which is measured employing the aqueous solution containing the nucleic acid fragment sample.

In the present detection method, the specific base sequence of the DNA fragment (or PNA fragment) is preferably predetermined. The DNA chip (or PNA chip) employed in the detection method of the invention preferably has a plurality of short chain spacer molecules having a hydrophilic moiety at each one end which are fixed at each another end onto a surface area of the electroconductive substrate having no DNA fragments (or no PNA fragments) thereon. The electrochemical thread intercalator preferably is a ferrocene-containing thread intercalator having an oxidative-reductive activity.

The measurement of the electric current in each step in the detection method of the invention is preferably conducted by differential pulse voltamography.

DETAILED DESCRIPTION OF THE INVENTION

Figure 1A:
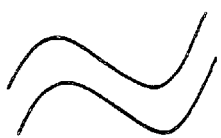
FIG. 1A and FIG. 1B schematically shows procedures of a known SSCP method.
Figure 1A:
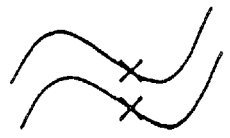
Figure 1A:
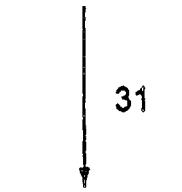
Figure 1A:
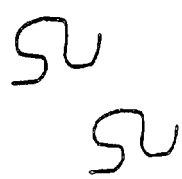
Figure 1A:
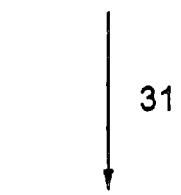
Figure 1A:
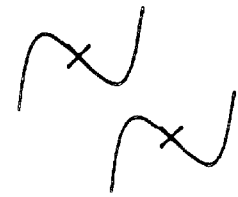
Figure 1B:
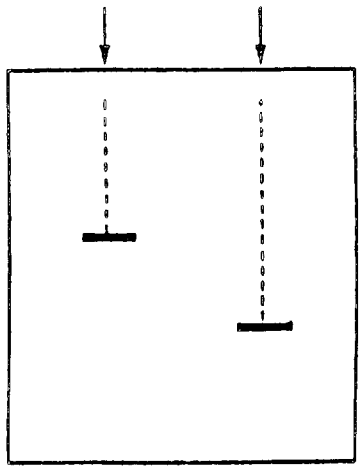

The DNA chip and PNA chip preferably employed in the detection method of the invention are described below. Since the DNA chip and PNA chip have essentially the same structure, the following description is mainly addressed to the structure and preparation of the DNA chip.

[Electroconductive Substrate]

The DNA chip employed in the invention generally has an electroconductive substrate (eg, electrode).

The electroconductive substrate may be provided on an electro-insulative support material. The electroconductive substrate and the support material preferably have a less hydrophilic surface or a hydrophobic surface. The electroconductive substrate may have a plain surface or a surface having many fine concaves and convexes.

The electro-insulative support material can be prepared from glass, ceramics, polymer materials (e.g., polyethylene terephthalate, cellulose acetate, polycarbonate of Bisphenol A, polystyrene, poly(methyl methacrylate), silicon, active carbon, and porous materials (e.g., porous glass, porous ceramics, porous silicon, porous active carbon, cloth, knitted cloth, non-woven cloth, filter paper, and membrane filter). Polymer materials, glass, and silicon are preferably employed.

Generally, the electro-insulative support material is employed in the form of a sheet (or a film). The sheet of the support material preferably has a thickness in the range of 100 to 1,000 $\mu$m.

The electroconductive substrate can be made of electrode material, optical fiber, photodiode, thermistor, piezo electrical element, or surface elasticity element. The electrode material is generally employed. The electrode can be carbon electrode of graphite or glassy carbon, noble metal electrode of platinum, gold, palladium, or rhodium, metal oxide electrode of titanium dioxide, tin oxide, manganese oxide, or lead oxide, semiconductor electrode of Si, Ge, ZnO, or Cds, or electron conductor of titanium. Preferred are glassy carbon electrode and gold electrode. The electrode may be covered with electroconductive polymer film or monomolecular film.

The DNA chip of the invention is preferably composed of a hydrophobic, electro-insulative support material, a plurality of hydrophobic electroconductive substrates placed on the support material, a plurality of DNA fragments fixed on each of the electroconductive substrates, and, optionally, a plurality of spacer molecules fixed on the substrates at free areas (i.e., areas where no DNA fragments are present). Each of the electroconductive substrates is preferably arranged apart from the adjoining electroconductive substrates so that each substrate is insulated from the adjoining substrates. The electro-conductive substrate may be placed on the support material via an intermediate layer such as a hydrophilic intermediate layer which may have electron charges.

An example of the structure composed of an electroinsulative support material and a plurality of electrodes arranged on the support material is a silicon chip described in Sosnowski, R. G, et al., Proc. Natl. Acad. USA, 94, 1119–1123 (1997). The electrode may be produced on a polymer film using a composite sheet of a polymer film and a metal film.

[DNA Fragment]

As is described before, the detection method of the invention is preferably employed for detecting an abnormal gene fragment having one or more different bases from its corresponding normal gene fragment. Accordingly, the normal gene fragment or the abnormal gene fragment is preferably employed as the DNA fragment (DNA probe) to be fixed on the electroconductive substrate. It is preferred that the normal gene fragment is used as the DNA probe.

Otherwise, DNA fragment to be fixed onto the electroconductive substrate may be oligonucleotide, which is favorably employed for studying variations and polymorphism of gene. The DNA fragment to be fixed onto the substrate preferably is one of 3 to 50 mers, more preferably 10 to 25 mers.

If the DNA chip of the invention comprises plural DNA chip units each of which has an electroconductive substrate (e.g., electrode) and DNA fragments fixed onto the substrate, the plural DNA chip units can have the same DNA fragments or different DNA fragments.

Fixation of DNA fragments onto the substrate can be done by any of known methods. For instance, DNA fragments having a reactive group on one end can be fixed onto the substrate through covalent bond by the reaction of the reactive group and the functional group of the surface of the substrate. For instance, a mercapto group is attached to DNA fragment at its 5'- or 3'-terminal, and the mercapto group is then caused to react with a gold electrode, so that an electroconductive substrate having DNA fragments fixed thereon is produced. The procedure for attaching a mercapto group to DNA fragments is described in M. Maeda, et al., Chem Lett, 1805–1808(1994) and B. A. Connolly, Nucleic Acids Res., 13, 4484(1985).

If the electroconductive substrate is made of glassy carbon electrode, the glassy carbon electrode is oxidized by potassium permanganate to produce a carboxylic acid group on the electrode. The carboxylic acid group on the electrode forms an amide bonding with DNA fragment so that the DNA fragment is fixed onto the Citrate. See K. M. Millan, et al., Analytical Chemistry, 65, 2317–2323(1993).

DNA fragments can be fixed to the substrate, initially, in the form of hybrid DNA fragments. For instance, the hybrid DNA fragments are combined with a mercapto group at their 5'- or 3'-terminals (preferably 5'-terminals) of their single fragment, and are brought into contact with a gold electrode, so that the hybrid DNA fragments are fixed on the electrode. The hybrid DNA fragment fixed on the electrode is then processed to dissociate a single fragment having no mercapto group, so that the desired DNA chip is produced.

The covalent bond between the DNA fragment and the substrate can be formed using an amino group, an aldehyde group, a mercapto group, or a biotin molecule which is attached to the DNA fragment.

Otherwise, DNA fragments can be synthesized on the substrate by a known method.

The DNA fragment having a reactive group on one end can be fixed onto an electroconductive substrate by spotting onto the substrate an aqueous solution containing the DNA fragment. The aqueous solution preferably contains the DNA fragment in a concentration of several pM to several mM. The volume for the spotting generally is in the range of 1 to 100 nL, preferably 1 to 10 nL. The aqueous solution may contain a viscosity increasing additive such as sucrose, polyethylene glycol, or glycerol. The spotting can be made manually or utilizing a commercially available spotter. The spotted solution is then kept on the electroconductive substrate at a predetermined temperature for several hours (namely, incubation), whereby the DNA fragment is fixed onto the substrate by covalent bonding After the incubation is complete, free DNA fragment (which is not fixed onto the substrate) is preferably washed out.

The DNA fragment is preferably fixed onto the electroconductive substrate in an amount of $10^{-20}$ to $10^{-12}$ mol./$mm^2$ of the surface area of the substrate. The amount of the fixed DNA fragment can be determined by means of HPLC (high performance liquid chromatography) or other analytical apparatuses.

[PNA Fragment]

The PNA fragment preferably employable in the invention has the following formula (I):

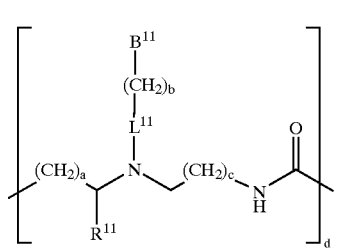

(I)

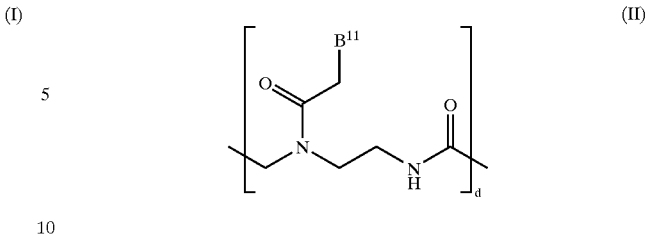

(II)

In the formula, the symbols of $B^{11}$, $R^{11}$, $L^{11}$, a, b, c, and d have the meanings described below.

$B^{11}$ is a ligand and represents one of bases of natural nucleic acids (i.e., A, T, C, G, I, or U) or its analogue. $B^{11}$ is bonded through the 9th position in the case that the base is a purine base such as adenine, guanine or inosine, and through the 1st position in the case that the base is a pyrimidine base such as thymine, uracil or cytosine. The base analogue is an organic base which is similar to the base of natural origin in its chemical structure, for instance, a base group which is prepared by replacing the carbon or nitrogen atom of the purine or pyrimidine ring with a nitrogen or carbon atom, respectively, or a base group modifying the purine or pyrimidine ring with a substituent such as a sulfhydryl group or a halogen atom. Otherwise, $B^{11}$ can be an aromatic moiety containing no nucleic acid base, an alkanoyl group having 1 to 4 carbon atoms, a hydroxyl group, or a hydrogen atom. Examples of the base analogues include 7-deazaadenine, 6-azauracil, and 5-azacytosine. $B^{11}$ also can be a DNA intercalator, a reporter ligand, a protein label such as hapten or biotin, a spin label, or a radioactive label. Particularly preferred are nucleic acid bases (i.e., A, T, C, G, and U).

$R^1$ is a hydrogen atom or a group derived from a sidechain of an α-amino acid of natural origin. Examples of such groups include an alkyl group having 1 to 6 carbon atoms, an aryl group having 6 to 20 carbon atoms, an aralkyl group having an alkyl group of 1 to 6 carbon atoms, a heteroaryl group having 6 to 20 carbon atoms, a hydroxyl group, an alkoxy group having 1 to 6 carbon atoms, an alkylthio group having 1 to 6 carbon atoms, a group of —$NR^{13}R^{14}$ [each of $R^{13}$ and $R^{14}$ independently is a hydrogen atom, an alkyl group having 1 to 3 carbon atoms, an alkoxy group having 1 to 3 carbon atoms, an alkylthio group having 1 to 3 carbon atoms, or a hydroxyl group], and a mercapto group. $R^{11}$ may form an alicyclic ring or a heterocyclic ring in combination with the carbon atom to which $R^{11}$ is attached.

$L^{11}$ is a linking group such as a divalent group represented by the group of —CO— or —$CONR^{12}$—[$R^{12}$ is a hydrogen atom, an alkylene group having 1 to 4 carbon atoms, a hydroxyl group, an alkoxy group having 1 to 4 carbon atoms, or an amino group], or an alkylene group having 1 to 4 carbon atoms. The alkoxy group and amino group way have one or more substituents such as alkyl of 1–4 carbon atoms, alkoxy of 1–4 carbon atoms, and hydroxyl.

Each of a, b and c independently is an integer of 0 to 5, preferably 1, and d is an integer of 1 to 60, preferably an integer of 1 to 40.

A particularly preferred PNA fragment has the following formula (II), in which each of $B^{11}$ and d has the same meaning as described above for the formula (I):

The PNA fragment can be fixed onto an electroconductive substrate in a known manner (see Protein, Nucleic Acid, Enzyme, Vol.43, No.13, 2004–2011(1988) and Japanese Patent Provisional Publication 9-288080. Also employable are procedures similar to the aforementioned DNA fragment-fixing procedures.

[Short Chain Spacer Molecules]

The DNA chip preferably has a plurality of short chain spacer molecules having a hydrophilic moiety at each one end which are fixed at each another end onto a surface area of the electroconductive substrate having no DNA fragments thereon. The coverage of the substrate using the spacer molecules can be expressed in terms of "masking treatment".

The short chain of the spacer molecule means that the molecular length of the spacer molecule is sufficiently short, as compared with the length of the DNA fragment fixed onto the substrate in their vicinity.

The spacer molecule preferably has a main skeleton composed of an alkylene group having 1 to 6 carbon atoms. The spacer molecule may have a cyclic group in the molecular chain or as a substituent Examples of the cyclic groups include an aryl group having 6 to 12 carbon atoms, a cycloalkyl group having 3 to 6 carbon atoms, and a heterocyclic group containing 1 to 4 hetero atoms (eg., N, S, O, or P) and 2 to 20 carbon atoms. The cyclic group can contain the reactive group which can be reacted with the substrate surface to fix the spacer atoms to the substrate. One example is a imidazole-2-thione group.

The hydrophilic moiety can be attached to the spacer molecule in the terminal position or in the vicinity of the terminal position. One or more hydrophilic moieties may be attached to the spacer molecule. Examples of the hydrophilic moieties include hydroxyl, carboxyl, amido, phosphoryl, and sulfonyl. Preferred is hydroxyl.

The other end of the spacer molecule is fixed onto a surface area of the substrate where the DNA fragment is not attached. The fixation of the spacer molecule is preferably performed utilizing a reactive group which is attached to the spacer molecule at the other end. Examples of the reactive groups include mercapto, sulfide, disulfide, thiocarbonyl, and thiocarboxyl. Preferred are mercapto, thiocarbonyl, and sulfide. Most preferred is mercapto. It is also preferred that the electroconductive electrode has a reactive group, on its surface, such as amino, imino, hydrazino, hydrazide, amide, carboxyl, aldehyde, epoxy, or peroxy.

Examples of the reactive compounds serving as the spacer molecules include mercaptomethanol, 2-mercaptoethanol, 3-mercaptopropanol, 4-mercaptobutanol, 5-mercaptopentanol, 6-mercaptohexanol, N,N'-di(3-hydroxy-n-propyl)imidazole-2-thione, and various imidazole-2-thione derivatives described in A. J Arduengo, et al., J. Am. Chem. Soc, 1990, 112, 6153–6154. Preferred are 2-mercaptoethanol, 3-mercaptopropanol, 4-mercaptobutanol, 5-mercaptopentanol, and 6-mercaptohexanol. Most preferred is 2-mercaptoethanol. These active compounds may be in the form of their salts with sodium or potassium. The alkylene chain of the active compound can be substituted with one or more substituents such as a hydrocarbyl group having 1 to 6 carbon atoms (e.g., methyl, ethyl, or phenyl).

Onto the electroconductive substrate, two or more different spacer molecules can be provided.

[Hybridization]

The hybridization can be performed essentially in the same manner as that employed in various assay procedures utilizing the conventional DNA chip.

When the electrochemical analysis is performed, an electrochemically active molecule, specifically, an electrochemically active thread intercalator, is preferably employed for insertion into a hybrid formed by the DNA fragment and a sample nucleic acid fragment on the electroconductive substrate. The thread intercalator assists easy flowing of electric current from or to the substrate along the formed hybrid structure. The electrochemical thread intercalator can be present when hybridization takes place. Otherwise, the thread intercalator can be brought into contact with a previously formed hybrid structure. In the latter case, a free nucleic acid fragment which is not hybridized with the fixed DNA fragment is preferably removed from the substrate by washing with a mixture of a surfactant (preferably sodium dodecylsulfate) and a buffer (preferably a citrate buffer) in advance of the contact with the intercalator. The intercalator is preferably brought into contact with the hybrid in an aqueous solution at a concentration of 10 nM to 10 mM.

The hybridization is preferably performed at a temperature between room temperature and approximately 70° C., for 0.5 to 20 hours.

[Electrochemically Active Thread Intercalator]

The electrochemically active thread intercalators favorably employed for the electrochemical analysis of nucleic acid fragments are already known. A representative example of the intercalator is a thread intercalator having an electroconductive group at one end or both ends. The thread intercalator having the electroconductive group preferably has an oxidative-reductive activity. The oxidative-reductive activity can be imparted to the thread intercalator by incorporating into the intercalator a ferrocene group, a catechol amine group, a metal bipyridine complex group, a metal phenathroline complex group, or a viologen group. The intercalator moiety preferably comprises a naphthaleneimide moiety, an anthracene moiety, or an anthraquinone moiety. Preferred electrochemically active thread intercalator is a ferrocene containing naphthalene diimide compound [NDIFc$_2$-1, which is prepared from carboxylic acid ester of N-hydroxysuccinimide and a corresponding amine compound, see S. Takenaka et al., J. Chem. Soc. Commun., 1111 (1998))]:

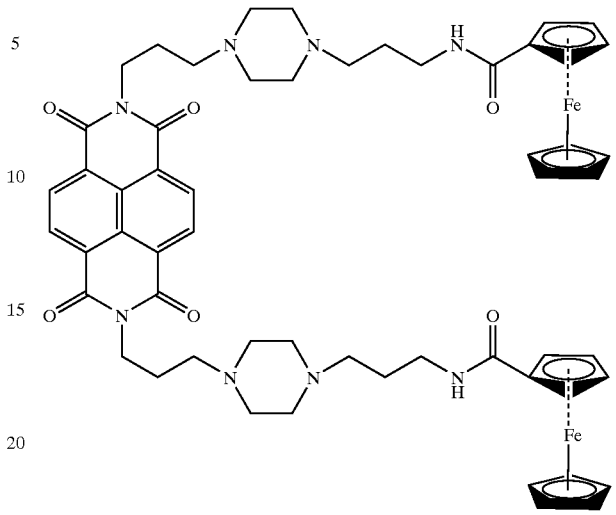
(NDIFc$_2$-1)

A ferrocene-containing naphthalene diimide derivative having the following formula is also preferably employed:

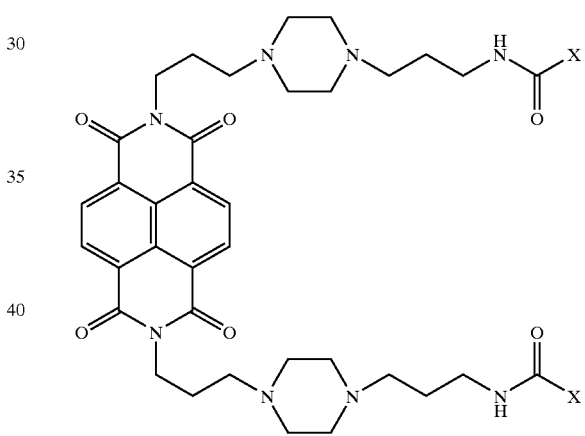

In the above-illustrated formula: X is one of the following ferrocene derivative groups:

(X1)

(X2)

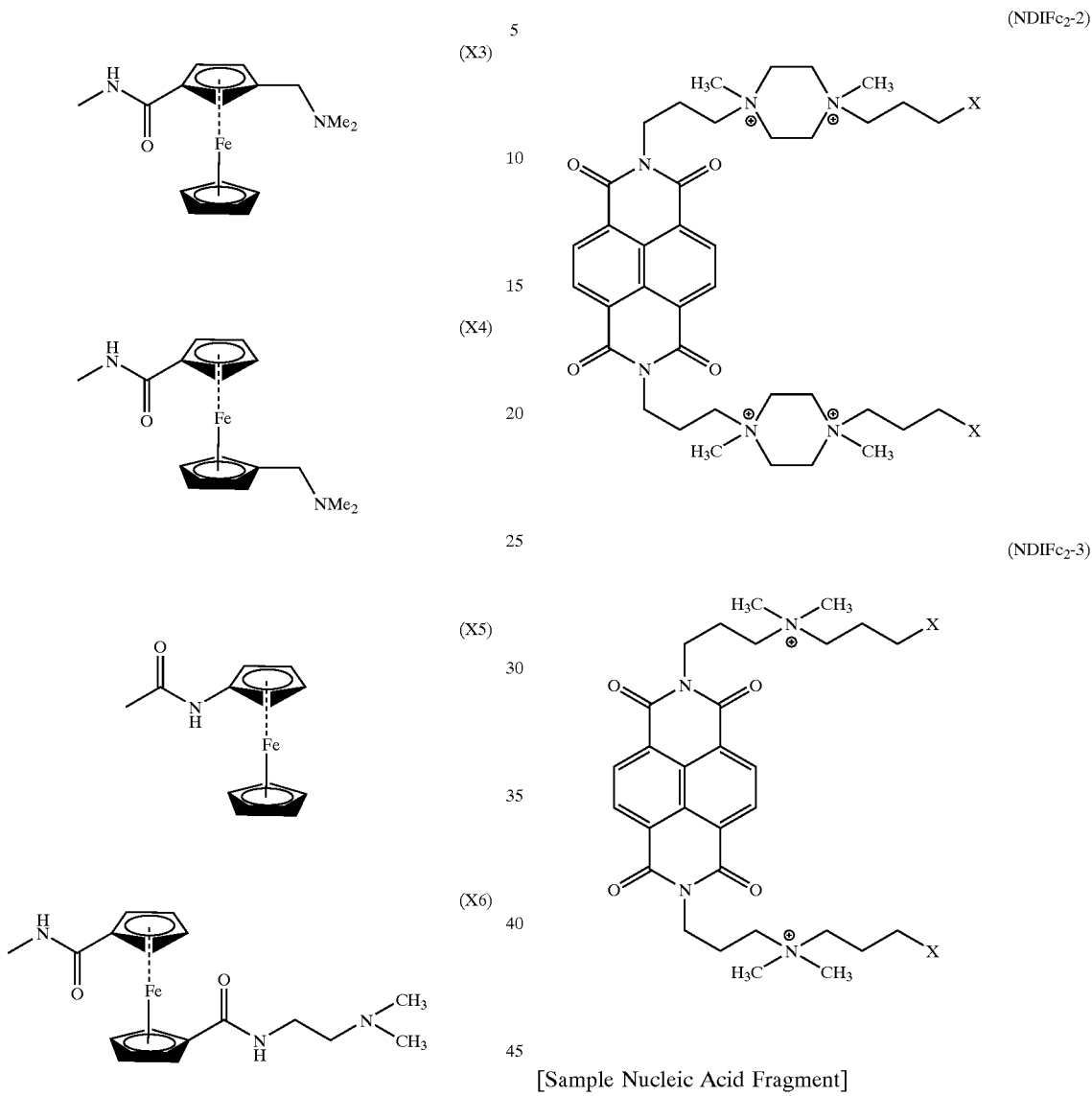

[Sample Nucleic Acid Fragment]

The thread intercalator having an electroconductive group comprises not only the oxidative-reductive active moiety and the intercalator moiety but also a linker moiety placed between these moieties. The 1,4-dipropyl-piperazinyl group of the formula is an example of the linker moiety. The piperazinyl group can be replaced with an quaternary imino group An intercalator of the below-illustrated formula which has a quaternary imino group always is cationic regardless of pH condition. This means that the intercalator is firmly fixed to the DNA hybrid and PNA hybrid. Accordingly, it is favorably employed in the invention. Particularly, the intercalator having a quaternary imino group is preferred in the use in combination with the PNA chip. The linker can be an N-alkyl group having 1 to 6 carbon atoms (e.g., methyl, ethyl, or n-propyl). The oxidative-reductive potential of the ferrocene moiety of the intercalator varies depending upon the nature of the linker moiety.

As is described before, the detection method of the invention is preferably employed for detecting an abnormal gene fragment having one or more different bases from its corresponding normal gene fragment. Accordingly, the normal gene fragment or the abnormal gene fragment is preferably employed as the sample nucleic acid fragment. It is preferred that the abnormal gene fragment is used as the sample nucleic acid fragment.

The abnormal gene fragment can be defective and different from the corresponding normal gene fragment. Examples of the abnormal gene fragments include a gene fragment in which one or more base units are replaced with different base units, a gene fragment in which one or more base units are missing from the normal gene fragment, and a gene fragment in which one or more base units are added to the normal gene fragment.

The abnormal gene fragment is generally obtained from a living body having the double stranded abnormal gene. The double stranded abnormal gene is cleaved and treated in the conventional manner to give a single stranded abnormal gene fragment for performing the detection of the invention. The single stranded abnormal gene fragment can be chemically synthesized.

[Detection of Partly Complementary Nucleic Acid Sample]

Figure 2:
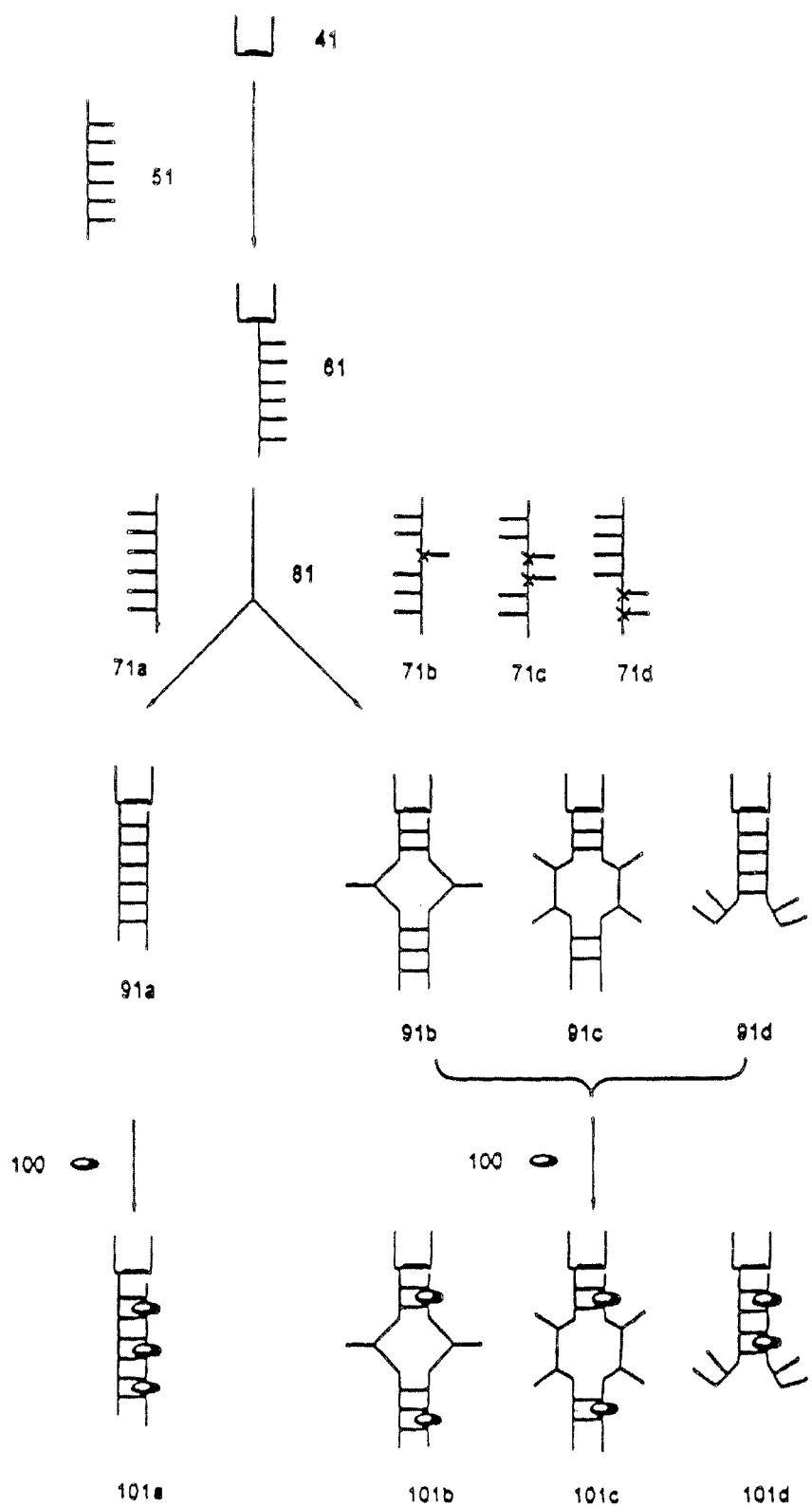
FIG. 2 schematically shows procedures of a typical detection method of the invention.

A method of the invention for analyzing a nucleic acid fragment sample to judge whether the nucleic acid fragment sample is uncomplementary, partly complementary or complementary to a DNA fragment in its specific base sequence is described by referring to FIG. 2.

The detection method of the invention typically comprises the following steps.

On an electroconductive substrate (41) is fixed a single stranded normal DNA fragment (51, namely DNA probe) to give a DNA chip (61). The DNA chip (61) is brought into contact with an aqueous solution containing a single stranded normal nucleic acid fragment (71a) which is completely hybridizable with the DNA fragment (51), an aqueous solution containing a single stranded abnormal nucleic acid fragment (71b) which is different from the fragment (71a) in one base unit, or an aqueous solution containing a single stranded abnormal nucleic acid fragment (71c or 71d) which is different from the fragment (71a) in two base units. The abnormal nucleic acid fragments (71b, 71c, 71d) differ from the normal nucleic acid fragment (71a) in the base unit or units at the crossed point.

Upon the contact, each of the fragments (71a, 71b, 71c, 71d) hybridizes with the DNA probe (51) to give a full-match hybrid structure (91a), a mis-match hybrid structure (91b), and bulge hybrid structures (91c, 91d), respectively. The full-match hybrid structure (91a) is the completely hybridized structure. The mis-match hybrid structure (91b) has a missing bond at one defective base unit The bulge hybrid structures (91c, 91d) has a missing bond at two defective base units.

These structures are brought into contact with an electrochemically active thread intercalator (100), to give various intercalator-containing hybrid structures (101a, 101b, 101c, 101d).

To the DNA chip having thereon one of these intercalator-containing hybrid structures in an aqueous solution is applied a potential, and an electric current flowing from or to the electroconductive substrate along the hybrid structure having the electrochemically active thread intercalator is measured. The same procedure is repeated using one or more other DNA chips having different hybrid structures to which the intercalator is attached.

The electric currents measured are then compared with each other. Apparently, the hybrid structure (91a, 101a) is most stable, as compared with the other hybrid structures (91b, 101b, 91c, 101c, 91d, 101d). This means that much electric current flows on the DNA chip having the hybrid structure (91a, 101a) formed with the normal DNA fragment (71a), as compared with other DNA chips having the other hybrid structures.

Accordingly, if the electric current measured on the DNA chip having the hybrid structure (91a, 101a) formed with the normal DNA fragment (71a) is employed as a control, DNA chips having the other hybrid structures can be detected by comparing the electric currents flowing on the DNA chips. The electric current measured on the DNA chip having the hybrid structure (91a, 101a) formed with the normal DNA fragment (71a) is previously or separately prepared.

The detection method of the invention may further comprises the steps for obtaining a background electric current data (i.e., blank data) and comparing the blank data with the electric current measured in the above-described step.

The additional comparing procedure can be performed by the steps of:

bringing an aqueous solution not containing the nucleic acid fragment sample into contact with a DNA chip equivalent of the DNA chip in the presence of the electrochemical thread intercalator;

measuring an electric current flowing from or to the electroconductive substrate along the DNA fragment under application of a potential to the substrate so as to obtain a background electric current; and comparing the background electric current with the electric current which is measured employing the aqueous solution containing the nucleic acid fragment sample.

The fixation of the electrochemically active thread intercalator to the hybrid structure can be detected by measuring an electric current flowing from or to the electroconductive substrate (i.e., electroconductive substrate) along the hybrid structure having the electro-chemically active thread intercalator. The measurement of electric current can be performed by any of known methods such as cyclic voltamography (CV), differential pulse voltamography (DPD), and potentiostat. The differential pulse voltamography is most preferred.

The present invention is further described by the following examples.

In the following Examples 2 to 4, the following terminology is used:

Oligonucleotide WT+: d(GTCGGACTGAAGA) ("SEQ ID NO 1") which is a sense chain of normal lipoprotein lipase (LPL) gene Oligonucleotide WT−: d(GAGCCTGACTTCT) ("SEQ ID NO 2") which is an anti-sense chain of the above LPL gene Oligonucleotide S447X+: d(GTCGGAG*TGAAGA) ("SEQ ID No 3") which is a sense chain of gene which is produced by change in the normal LPL gene from the 447$^{th}$ serine (TCA) to the termination codon (TGA)

Oligonucleotide S447X−: d(CAGCCTC*ACTTCT) ("SEQ ID No. 4") which is an antisense chain of the above-mentioned gene.

In the above base sequences, the base having "*" on its shoulder means a base changed from the normal base in the normal gene.

EXAMPLE 1-1

Detection of Partly Complementary Nucleic Acid Using a Synthetically Prepared Nucleic Acid Fragment Sample for the Formation of Mis-match Hybrid Structure (1) Preparation of DNA Chip A gold electrode (surface area: 2 mm$^2$) was immersed in an aqueous 2N sodium hydroxide solution for one hour, washed with super pure water, and immersed in conc. nitric acid The nitric acid was stirred for 15 min. The gold electrode was then washed with super pure water and dried. On thus treated gold electrode was spotted 1.0 μL of an aqueous solution containing 20 mers of adenine having a mercaptohexyl group at its 5'-terminal (HS-dA$_{20}$, in an amount of 10 pico mol./μL), and the electrode was allowed to stand for 2 hours. The electrode was washed with super pure water to give a DNA chip. The preparation of HS-dA$_{20}$ was made in the manner described in Japanese Patent Provisional Publication No. 9-288080.

The aqueous solution containing HS-dA$_{20}$ and an aqueous solution recovered after the spotting were subjected to high perforce liquid chromatography (HPLC) to measure change of the peak assigned to HS-dA$_{20}$, whereby determining the amount of the fixed HS-dA$_{20}$. It was confirmed that HS-dA$_{20}$ was fixed onto the gold electrode almost quantitatively.

(2) Fixation of Spacer Molecules

Onto the DNA chip prepared in (1) above was spotted 1 μL of an aqueous 2-mercaptoethanol solution (1 mM). The spotted solution was covered and allowed to stand for 2 hours. The DNA chip was then washed with super pure water, to give the DNA chip having spacer molecules on its electrode.

(3) Preparation of Sample Nucleic Acid Fragment

A nucleic acid fragment of the following dT$_9$dAdT$_{10}$ was prepared in the manner described in the above-mentioned patent publication:
5'-TTTTTTTTTTATTTTTTTTT-3' (SEQ ID NO 5")

(4) Synthesis of Ferrocene-containing Thread Intercalator

The below-illustrated ferrocene-containing naphthalene diimide was synthesized in the manner described in the above-mentioned patent publication:

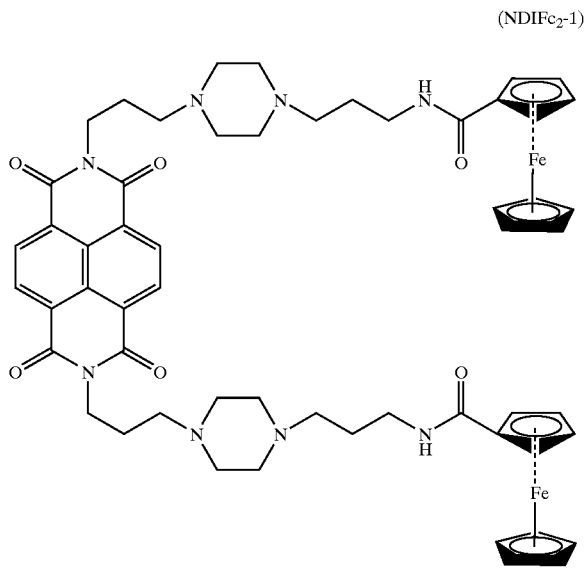

(NDIFc$_2$-1)

(5) Hybridization Between DNA Chip and Sample Nucleic Acid Fragment

One μL of an aqueous solution containing 20 pico mol./μL of dT$_9$dAdT$_{10}$ prepared in (3) above was spotted on the DNA chip, and the spotted chip was allowed to stand at 20° C. for 30 min, for incubation.

(6) Measurement of Electric Current

An aqueous electrolytic solution [mixture of aqueous 0.1 M acetic acid/potassium acetate solution (pH 5.6) and aqueous 0.1 M potassium chloride solution) containing 50 μM of the ferrocene-containing naphthalene diimide (prepared in (4) above)] was placed in a thermostat cell maintained at 20° C. In the aqueous electrolytic solution were placed tri-electrodes composed of the DNA chip (i.e., working electrode), a platinum electrode (opposite electrode), and a silver/silver chloride referential electrode), and differential pulse voltamography (DPV) was performed at 42° C.

Figure 3:
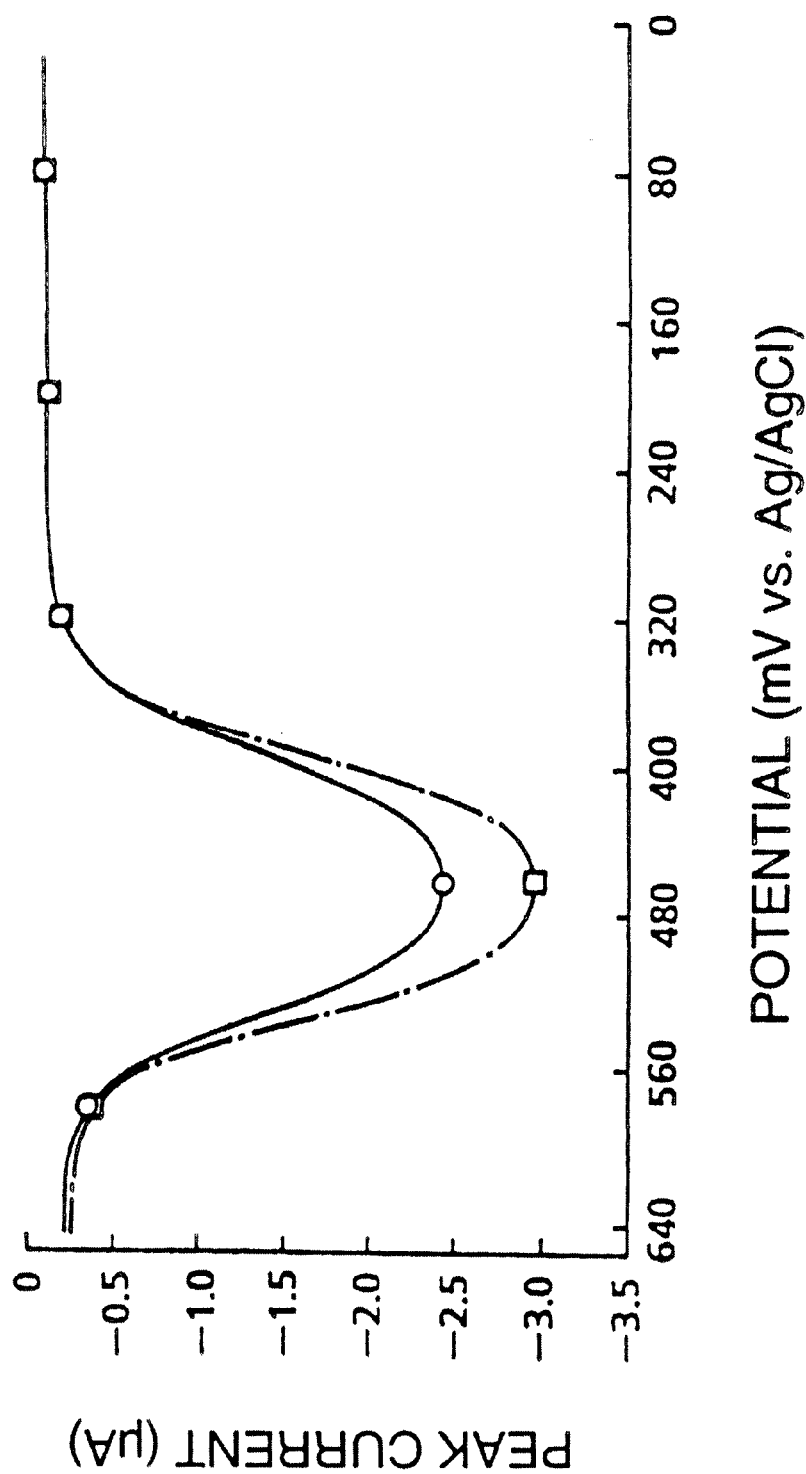
FIG. 3 graphically shows results of differential pulse voltamography given in the detection of hybridization of HS-dA$_{20}$ and dT$_9$dAdT$_{10}$ and differential pulse voltamography for HS-d$_{20}$ only.

FIG. 3 indicates the voltamography data (DVP-2) for the mis-match hybrid structure by the chain curve connecting the blank squares.

The above-mentioned detection procedures were repeated using aqueous solutions containing no sample nucleic acid fragment, for comparison. FIG. 3 indicates the voltamography data (DVP-1) by the curve connecting the circles.

The peak current at 460 mV of DPV-2 is higher than the corresponding peak current of DPV-1 by 22.2%.

EXAMPLE 1-2

Figure 4:
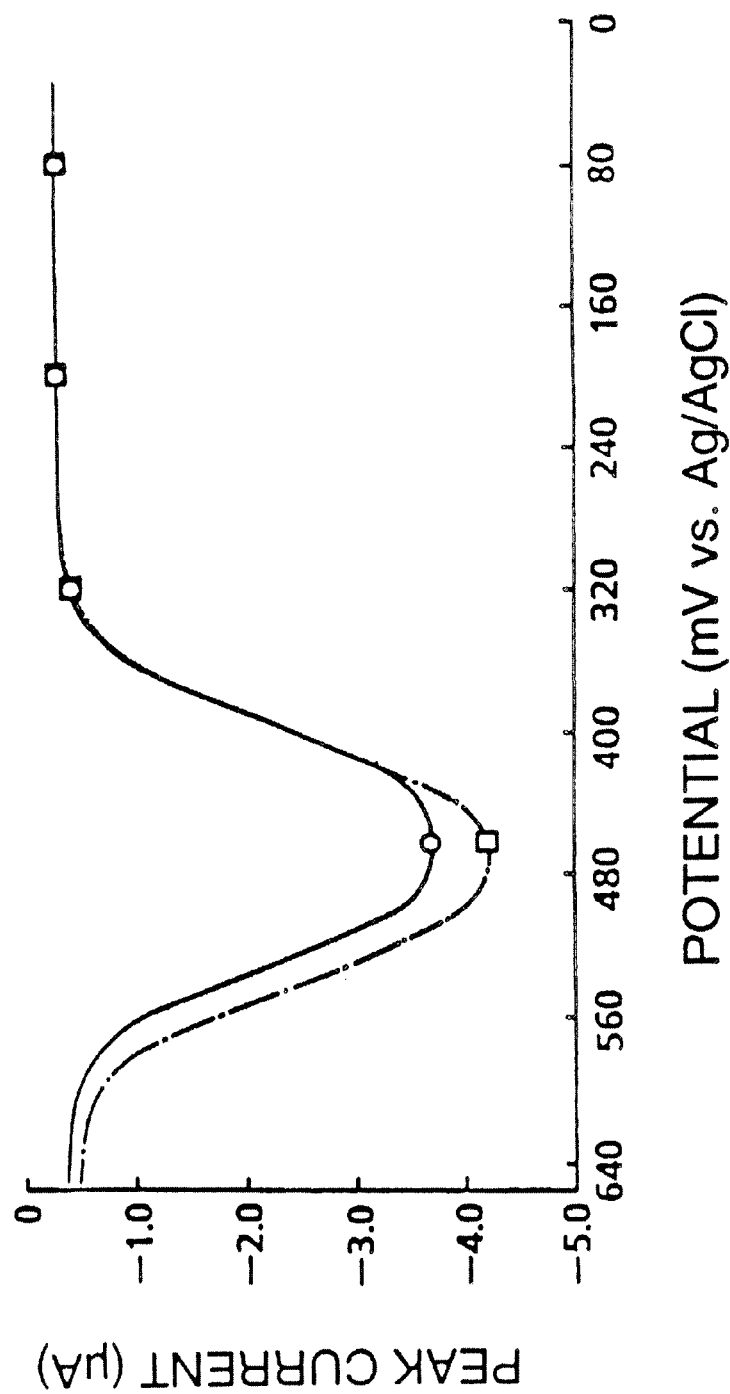
FIG. 4 graphically shows results of differential pulse voltamography given in the detection of hybridization of HS-dA$_{20}$ and dT$_8$dPdT and differential pulse voltamography for HS-dA$_{20}$ only.

Detection of Partly Complementary Nucleic Acid Using a Synthetically Prepared Nucleic Acid Fragment Sample for the Formation of Bulge Hybrid Structure The procedures of Example 1-1 were repeated except for replacing the sample nucleic acid fragment with the following dT$_8$dA$_4$dT$_8$ to obtain a bulge hybrid structure of a voltamographic curve of DPV-4 represented by—blank square—in FIG. 4:
5'-TTTTTTTTAAAATTTTTTTT-3' (SEQ ID NO 6")

Also repeated was the procedure using an aqueous solution containing no sample nucleic acid fragment to obtain a voltamographic curve of DPV-3 represented by—circle—in FIG. 4.

The peak current at 460 mV of DPV-4 is higher than the corresponding peak current of DPV-3 by 15.1%.

EXAMPLE 1-3

Figure 5:
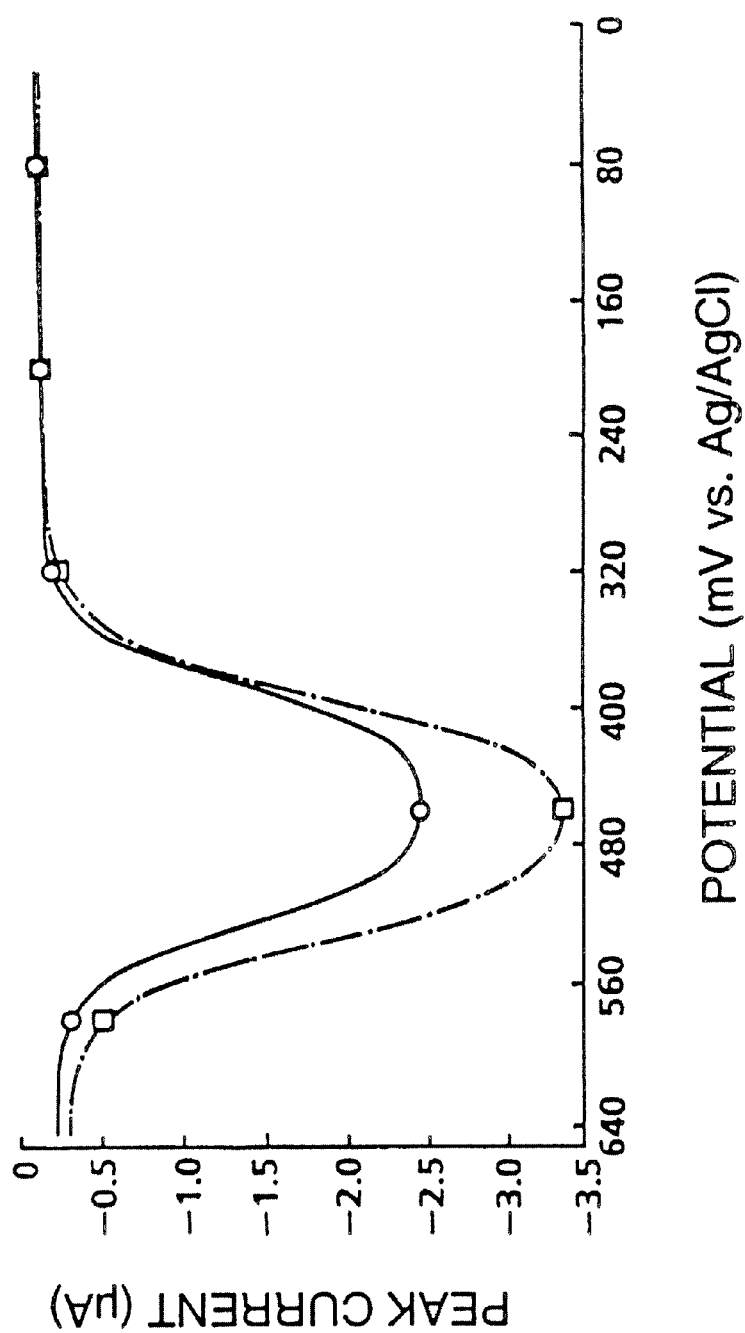
FIG. 5 graphically shows results of differential pulse voltamography given in the detection of hybridization of HS-dA$_{20}$ and dT$_{20}$ and differential pulse voltamography for HS-dA$_{20}$ only.

Detection of Complementary Nucleic Acid Using a Synthetically Prepared Nucleic Acid Fragment Sample for the Formation of Full-match Hybrid Structure The procedures of Example 1-1 were repeated except for replacing the sample nucleic acid fragment with the thymine 20 mers (dT$_{20}$) to obtain a full-match hybrid structure of a voltamographic curve of DPV-6 represented by—blank square—in FIG. 5.

Also repeated was the procedure using an aqueous solution containing no sample nucleic acid fragment to obtain a voltamographic curve of DPV-5 represented by—circle—in FIG. 5.

The peak current at 460 mV of DPV-6 is higher than the corresponding peak current of DPV-5 by 37.3%.

EXAMPLE 2-1

Detection of Partly Complementary Nucleic Acid Using a LPL Abnormal Gene Fragment Sample for the Formation of Mis-match Hybrid Structure (1) Preparation of DNA Chip The preparation of procedures of DNA chip described in Example 1-1 were repeated except for using an aqueous solution of 10 pico mol. Of HS-d(CAGCCTGACTTCT) ("SEQ ID NO.2") having a mercaptohexyl group at 5'-terminal of oligonucleotide WT–, to prepare a DNA chip. The oligonucleotide was prepared in the manner described in the aforementioned patent publication.

(2) Preparation of Sample Nucleic Acid Fragment

S447X+ (a model gene of a LPL abnormal gene) was prepared in the manner described in the aforementioned patent publication.

(3) Hybridization and Measurement of Electric Current

The corresponding procedures of Example 1-1 were repeated except for using the DNA chip prepared in (1) above and the sample nucleic acid fragment prepared in (2) above, to obtain a mis-match hybrid structure of a voltamographic curve of DPV-8.

Also repeated was the procedure using an aqueous solution containing no sample nucleic acid fragment to obtain a voltamographic curve of DPV-7.

The peak current at 460 mV of DPV-8 differs from the corresponding peak current of DPV-7 by 6.3%.

EXAMPLE 2-2

Detection of Complementary Nucleic Acid Using a LPL Normal Gene Fragment Sample for the Formation of Full-match Hybrid Structure The corresponding procedures of Example 2-1 were repeated except for using the sample nucleic acid fragment of oligonucleotide WT+, to obtain a full-match hybrid structure of a voltamographic curve of DPV-10.

Also repeated was the procedure using an aqueous solution containing no sample nucleic acid fragment to obtain a voltamographic curve of DPV-9.

The peak current at 460 mV of DPV-10 differs from the corresponding peak current of DPV-9 by 65.4%.

EXAMPLE 3-1

Detection of Partly Complementary Nucleic Acid Using a LPL Abnormal Gene Fragment Sample for the Formation of Mis-match Hybrid Structure
(1) Preparation of DNA Chip The preparation procedures of DNA chip described in Example 1-1 were repeated except for using an aqueous solution of 10 pico mol. Of HS-d (CAGCCTCACTTCT) (SEQ ID NO 2) having a mercaptohexyl group at 5'-terminal of oligonucleotide S447X-, to prepare a DNA chip. The oligonucleotide was prepared in the manner described in the aforementioned patent publication.
(2) Hybridization and Measurement of Electric Current The corresponding procedures of Example 1-1 were repeated except for using the DNA chip prepared in (1) above and the sample nucleic acid fragment of nucleotide WT+, to obtain a mis-match hybrid structure of a voltamographic curve of DPV-12.

Also repeated was the procedure using an aqueous solution containing no sample nucleic acid fragment to obtain a voltamographic curve of DPV-11.

The peak current at 460 mV of DPV-12 differs from the corresponding peak current of DPV-11 by 97%.

EXAMPLE 3-2

Detection of Complementary Nucleic Acid Using a LPL Normal gene Fragment Sample for the Formation of Full-match Hybrid Structure The corresponding procedures of Example 3-1 were repeated except for using the sample nucleic acid fragment of oligonucleotide S447X+, to obtain a full-match hybrid structure of a voltamographic curve of DPV-14.

Also repeated was the procedure using an aqueous solution containing no sample nucleic acid fragment to obtain a voltamographic curve of DPV-13.

The peak current at 460 mV of DPV-14 differs from the corresponding peak current of DPV-13 by 29.4%.

EXAMPLE 4-1

Detection of Partly Complementary Nucleic Acid Using a LPL Abnormal Gene Fragment Sample
(1) Preparation of DNA Chip The preparation procedures of DNA chip described in Example 1-1 were repeated except for using an aqueous solution of 2 pico mol./µL of oligonucleotide WT-, to prepare a DNA chip.

(2) Preparation of Sample Nucleic Acid Fragment

A PLP gene portion of a chromosome DNA obtained by purification of leucocyte (1 mL) of a patient having abnormal LPL gene was multiplied (40 cycles) by PCR method to obtain oligonucleotide S447+/S447X+. The obtained oligonucleotide was purified by dialysis to prepare a sample nucleic acid fragment for hybridization.
(3) Hybridization and Measurement of Electric Current The corresponding procedures of Example 1-1 were repeated except for using the DNA chip prepared in (1) above and the sample nucleic acid fragment of (2) above, to obtain a partly complementary hybrid structure of a voltamographic curve of DPV-16.

Also repeated was the procedure using an aqueous solution containing no sample nucleic acid fragment to obtain a voltamographic curve of DPV-15.

The peak current at 460 mV of DPV-16 adversely differs from the corresponding peak current of DPV-15 by 1.4%.

EXAMPLE 4-2

Detection of Partly Complementary Nucleic Acid Using a LPL Abnormal/normal Mixed Gene Fragment Sample
(1) Preparation of Sample Nucleic Acid Fragment A PLP gene portion of a chromosome DNA obtained by purification of leucocyte (1 mL) of a patient having normal LPL gene was multiplied (40 cycles) by PCR method to obtain oligonucleotide WT+/WT+. The obtained oligonucleotide WT+/WT+was combined with the oligonucleotide S447X+/S447X+obtained in Example 4-1 at a ratio of 1:1, and purified by dialysis to prepare a sample nucleic acid fragment for hybridization.
(2) Hybridization and Measurement of Electric Current The corresponding procedures of Example 4-1 were repeated except for using the sample nucleic acid fragment of (1) above, to obtain a partly complementary hybrid structure of a voltamographic curve of DPV-18.

Also repeated was the procedure using an aqueous solution containing no sample nucleic acid fragment to obtain a voltamographic curve of DPV-17.

The peak current at 460 mV of DPV-18 differs from the corresponding peak current of DPV-19 by 16.4%.

EXAMPLE 4-3

Detection of Complementary Nucleic Acid Using a LPL Normal Gene Fragment Sample for the Formation of Full-match Hybrid Structure The corresponding procedures of Example 4-1 were repeated except for using the sample nucleic acid fragment of oligonucleotide WT+/WT+, to obtain a full-match hybrid structure of a voltamographic curve of DPV-20.

Also repeated was the procedure using an aqueous solution containing no sample nucleic acid fragment to obtain a voltamographic curve of DPV-19.

The peak current at 460 mV of DPV-20 differs from the corresponding peak current of DPV-19 by 38.4%.

SUMMARY OF EXAMPLE 1 to 4

The results of Examples 1 to 4 are summarized in Table 1.

TABLE 1

| Example | Probe DNA | Sample nucleic acid fragment | Variation of current |
|---|---|---|---|
| Example 1-1 | $dA_{20}$ | $dT_9dAdT_{10}$ | 22.2% |
| Example 1-2 | $dA_{20}$ | $dT_8dA_4dT_8$ | 15.1% |
| Example 1-3 | $dA_{20}$ | $dT_{20}$ | 37.3% |
| Example 2-1 | WT– | S447X+ | 6.3% |
| Example 2-2 | WT– | WT+ | 65.4% |
| Example 3-1 | S447X– | WT+ | 9.7% |
| Example 3-2 | S447X– | S447X+ | 29.4% |
| Example 4-1 | WT– | S447X+/S447X+ | –1.4% |
| Example 4-2 | WT– | WT+/S447X+ | 16.4% |
| Example 4-3 | WT– | WT+/WT+ | 38.4% |

The results of Example 1 to 4 indicate that the partly complementary nucleic acid fragments can be well detected by the method of the invention even if a hybrid structure is a mis-match structure or a bulge structure.

EXAMPLE 5

Relationship of Electric Current Variation and the Amount of Intercalator Attached to the Hybrid The hybridization and the measurement of electric current were performed in the same manner as in Example 1-1, except for varying the temperature for the measurement of DPV to 15° C., 25° C., 35° C., and 45° C. The DPV was then examined to determine a peak current at 450 mV and plotted in FIG. 6 by a blank triangle to give a chain curve.

The same procedures were repeated except for replacing the sample nucleic acid fragment to $dT_8dA_4dT_8$, to obtain the peak current. The results are plotted in FIG. 6 by a circle to give a solid curve. In this measurement, DPV was also obtained at 30° C.

Figure 6:
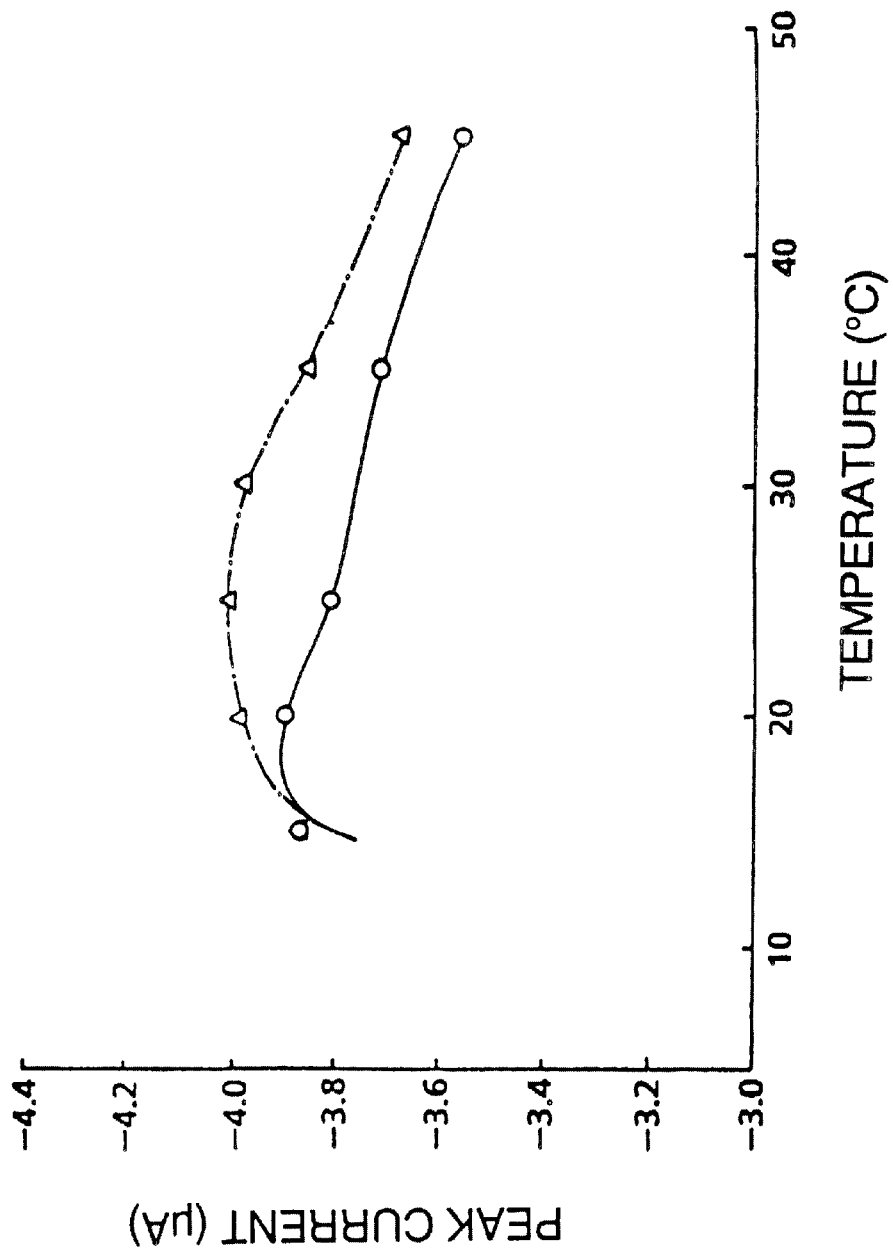
FIG. 6 illustrates a graph indicating variation of a peak electric current in a temperature variation which is obtained when HS-dA$_{20}$ and dT$_{20}$ are hybridized with each other, and a graph indicating variation of a peak electric current in a temperature variation which is obtained when HS-d$_{20}$ and dT$_8$dA$_4$dT$_8$ are hybridized with each other.

The results shown in FIG. 6 are understood to mean that the peak current corresponds to an amount of the thread intercalator attached to the hybrid structure, and does not correspond to the amount of formation of the hybrid structure on the electrode of the DNA chip. Further, it is understood that the hybridization is preferably performed at a low temperature around 20° C.

EXAMPLE 6-1

PNA Chip (1) Preparation of PNA Fragment

A PNA fragment (PNA-CTCT(C)$_2$(T)$_4$ ("SEQ ID NO. 7"), in which T stands for thymine, and C stands for cytosine] having the below-illustrated formula was prepared in the manner as described in P. E. Nielsen et al., Journal of American Chemical Society, 114, 1985–1897 (1992) and ibid., 114., 114, 9877–9678 (1992).

(2) Preparation of PNA Chip

On a gold electrode (surface area; 2.25 mm$^2$) having a mercapto group was spotted a phosphate buffer solution containing 1,2-bis(vinylsulfonylacetamide)ethane, to form a free vinylsulfonyl group on the electrode surface. On that surface was further spotted 2 μL of an aqueous solution of the above-mentioned PNA-CTCT (C)$_2$(T)$_4$ fragment (100 pico mol./1 μL solution). The spotted solution was allowed to stand for one hour at room temperature. The electrode was then-washed with distilled pure water to remove a free PNA fragment, whereby give a PNA chip.

(3) Preparation of Sample Nucleic Acid Fragment (3) Preparation of sample nucleic acid fragment DNA-(a) $_4$GTAGAG ("SEQ ID NO. 8") was prepared in the manner described in Japanese Patent provisional Publication No. 10-288-80 to use as a sample nucleic acid fragment.

(4) Hybridization and Measurement of Electric Current 4-1: Measurement of Background Current An aqueous electrolytic solution [mixture of aqueous 0.1 M acetic acid/potassium acetate solution (pH 5.6) and aqueous 0.1 M potassium chloride solution) containing 50 μM of the ferrocene-containing naphthalene diimide (prepared in Example 1-1)] was placed in a thermostat cell maintained at 38° C. The differential pulse voltamography (DPV) was performed at a voltage varying from 100 mV to 700 mV. Subsequently, a responsive current value (back ground value) was measured at a voltage of 460 mM to give a back ground value of –1.3 μA. The measurement was performed at a pulse amplitude of 50 mV, a pulse width of 50 mS, and a scanning rate of 100 mV/sec.

4-2: Detection of Complementary Nucleic Acid Fragment

2 μL of a 10 EM tris buffer (pH 7.5) containing 70 pico mol. of DNA-(A)$_4$GTAGA (obtained in (3) above) was spotted on the PNA chip (prepared in (2) above). Then, incubation was performed at 25° C. for 30 min. Thus incubated PNA chip was washed with an aqueous 0.1 M sodium dihydrogen phosphate-disodium hydrogen phosphate solution (pH 7.0) to remove unreacted DNA-(A), GTAGAG. Subsequently, the responsive current value (i.e., current value for the hybrid of PNA probe and sample nucleic acid fragment) was determined to give –1.7 μA. The variation of the responsive current value from the background value was 31%.

The same procedures were repeated except for using a DNA chip having a spotted DNA-CTCT(C)$_2$(T)$_4$ in place of the PNA chip, to determine a background value and a responsive current value –2.5 μA and –3.0 μA were obtained, respectively. The variation of the responsive current value from the background value was 20%.

EXAMPLE 6-2

PNA Chip

A sample nucleic acid fragment of DNA-(A)$_4$(G)$_2$AGAG ("SEQ ID NO 9") which was prepared in the manner in

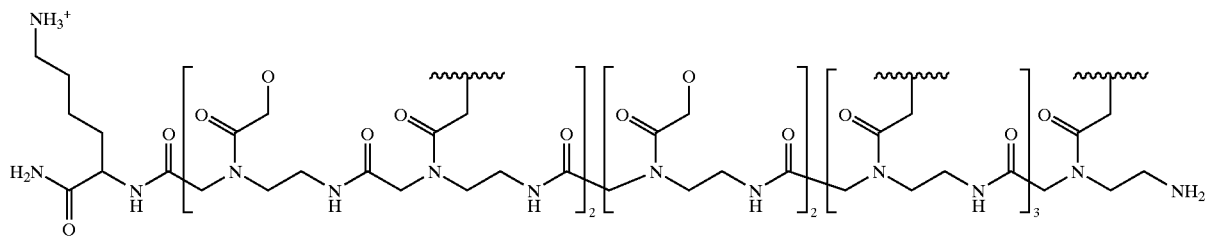

Japanese Patent Provisional Publication No. 10-288080 was spotted on the PNA chip prepared in Example 6-1. Subsequently, the procedures of (4) in example 6-1 were repeated to determine a background value and a responsive current value. −1.3 $\mu$A and −2.7 $\mu$A were obtained, respectively. The variation of the current value from the background value was 108%.

The same procedures were repeated except for using a DNA chip having a spotted DNA-CTCR(C)$_2$(T)$_4$ in place of the PNA chip, to determine a background value and a responsive current value. −2.5 $\mu$A and −3.5 $\mu$A were obtained, respectively. The variation of the responsive current value from the background value was 40%.

The results of Examples 6-1 and 6-2 indicate that the PNA chip is also effective to detect a partly complementary sample nucleic acid fragment and that the detection sensitivity is higher when the PNA chip is employed because the PNA chip gives a lower background value.

What is claimed is:

1. A method of analyzing a nucleic acid fragment sample to judge whether the nucleic acid fragment sample is uncomplementary, partly complementary or complementary to a DNA fragment in its specific base sequence, which comprises the steps of:

bringing an aqueous solution of the nucleic acid fragment sample into contact with a DNA chip comprising an electroconductive substrate and the DNA fragment fixed onto the substrate in the presence of an electrochemical thread intercalator having an electroconductive group at both ends;

measuring an electric current flowing from or to the electroconductive substrate along the DNA fragment under application of a potential to the substrate; and comparing the electric current measured above with a referential electric current which is prepared employing a combination of a DNA chip equivalent to the above-mentioned DNA chip, the electrochemical thread intercalator, and an aqueous solution of a nucleic acid fragment which is complementary to the DNA fragment of the DNA chip.

2. The method of claim 1, which further comprises the steps of:

bringing an aqueous solution not containing the nucleic acid fragment sample into contact with a DNA chip equivalent of the DNA chip in the presence of the electrochemical thread intercalator;

measuring an electric current flowing from or to the electroconductive substrate along the DNA fragment under application of a potential to the substrate so as to obtain a background electric current; and comparing the background electric current with the electric current which is measured employing the aqueous solution containing the nucleic acid fragment sample.

3. The method of claim 1, wherein the specific base sequence of the DNA fragment is predetermined.

4. The method of claim 2, wherein the specific base sequence of the DNA fragment is predetermined.

5. The method of claim 1, wherein the DNA chip has a plurality of short chainspacer molecules having a hydrophilic moiety at each one end which are fixed at each another end onto a surface area of the electroconductive substrate having no DNA fragments thereon.

6. The method of claim 2, wherein the DNA chip has a plurality of short chain spacer molecules having a hydrophilic moiety at each one end which are fixed at each another end onto a surface area of the electroconductive substrate having no DNA fragments thereon.

7. The method of claim 1, wherein the electrochemical thread intercalator is a ferrocene-containing thread intercalator having an oxidative-reductive activity.

8. The method of claim 2, wherein the electrochemical thread intercalator is a ferrocene-containing thread intercalator having an oxidative-reductive activity.

9. The method of claim 1, wherein the measurement of the electric current in each step is conducted by differential pulse voltamography.

10. The method of claim 2, wherein the measurement of the electric current in each step is conducted by differential pulse voltamography.

11. A method of analyzing a nucleic acid fragment sample to judge whether the nucleic acid fragment sample is uncomplementary, partly complementary or complementary to a PNA fragment in its specific base sequence, which comprises the steps of:

bringing an aqueous solution of the nucleic acid fragment sample into contact with a PNA chip comprising an electroconductive substrate and the PNA fragment fixed onto the substrate in the presence of an electrochemical thread intercalator having an electroconductive group at both ends;

measuring an electric current flowing from or to the electroconductive substrate along the PNA fragment under application of a potential to the substrate; and comparing the electric current measured above with a referential electric current which is prepared employing a combination of a PNA chip equivalent to the above-mentioned PNA chip, the electrochemical thread intercalator, and an aqueous solution of a nucleic acid fragment which is complementary to the PNA fragment of the PNA chip.

12. The method of claim 11, which further comprises the steps of:

bringing an aqueous solution not containing the nucleic acid fragment sample into contact with a PNA chip equivalent of the PNA chip in the presence of the electrochemical thread intercalator;

measuring an electric current flowing from or to the electroconductive substrate along the PNA fragment under application of a potential to the substrate so as to obtain a background electric current; and comparing the background electric current with the electric current which is measured employing the aqueous solution containing the nucleic acid fragment sample.

13. The method of claim 11, wherein the specific base sequence of the PNA fragment is predetermined.

14. The method of claim 12, wherein the specific base sequence of the PNA fragment is predetermined.

15. The method of claim 11, wherein the PNA chip has a plurality of short chain spacer molecules having a hydrophilic moiety at each one end which are fixed at each another end onto a surface area of the electroconductive substrate having no PNA fragments thereon.

16. The method of claim 12, wherein the PNA chip has a plurality of short chain spacer molecules having a hydrophilic moiety at each one end which are fixed at each another end onto a surface area of the electroconductive substrate having no PNA fragments thereon.

17. The method of claim 11, wherein the electrochemical thread intercalator is a ferrocene-containing thread intercalator having an oxidative-reductive activity.

18. The method of claim 12, wherein the electrochemical thread intercalator is a ferrocene-containing thread intercalator having an oxidative-reductive activity.

19. The method of claim 11, wherein the measurement of the electric current in each step is conducted by differential pulse voltamography.

20. The method of claim 12, wherein the measurement of the electric current in each step is conducted by differential pulse voltamography.

* * * * *